United States Patent [19]
Brown et al.

[11] Patent Number: 5,861,532
[45] Date of Patent: Jan. 19, 1999

[54] SOLID-PHASE SYNTHESIS OF N-ALKYL AMIDES

[75] Inventors: Edward G. Brown, Lafayette; John M. Nuss, Danville, both of Calif.

[73] Assignee: Chiron Corporation, Emeryville, Calif.

[21] Appl. No.: 813,019

[22] Filed: Mar. 4, 1997

[51] Int. Cl.$^6$ .................................................. C07C 231/02
[52] U.S. Cl. ......................... 564/142; 564/133; 564/134; 564/135; 564/136; 564/137; 564/139; 436/85; 436/86
[58] Field of Search ..................................... 564/133, 135, 564/136, 137, 139, 142; 436/85, 86

[56] References Cited

U.S. PATENT DOCUMENTS

| | | | |
|---|---|---|---|
| 4,531,000 | 7/1985 | Yalpani | 536/30 |
| 4,888,447 | 12/1989 | Smith | 564/480 |
| 5,508,400 | 4/1996 | Wilkerson et al. | 340/440 |

FOREIGN PATENT DOCUMENTS

| | | |
|---|---|---|
| 180455 A2 | 5/1986 | European Pat. Off. . |
| 405506 A1 | 1/1991 | European Pat. Off. . |
| 535731 A2 | 4/1993 | European Pat. Off. . |
| WO 92/20707 | 11/1992 | WIPO . |

OTHER PUBLICATIONS

Rink, Tetrahedron Letters, vol. 28, No. 33, pp. 3787–3790, 1987.
Boehm et al, J. Org. Chem., vol. 61, pp. 6498–6499, 1996.
Mokotoff et al, J. Med. Chem., vol. 35, pp. 4696–4702, 1992.
Sasaki and Coy, "Solid Phase Synthesis of Peptides Containing the $CH_2NH$ Peptide Bond Isosters" *Peptides* 8:119–121, 1987.
Breipohl et al., "Synthesis and Application of Acid Labile Anchor Groups for the Synthesis of Peptide Amides by Fmoc–Solid–Phase Peptide Synthesis" *Int. J. Peptides Res.* 34:262–267, 1989.
Mohan et al., "Synthesis and Biological Activity of Angiotensin II Analogues Containing a Val–His Replacement, Valψ[CH(CONH$_2$)NH]His" *J. Med. Chem.* 34:2402–2410, 1991.
Cushman and Oh, "Development of Metodology for the Synthesis of Stereochemically Pure Pheψ[CH$_2$N]Pro Linkages in HIV Protease Inhibitors" *J. Org. Chem.* 56:4161–4167, 1991.
Tourwé et al., "A New Method for the Solid Phase Synthesis of Hydroxyethlamine Peptide Bond Isosteres: Synthesis of an HIV–1 Protease Inhibitor and of a β–Casomorphin–5 Analogue" *Tetrahedron Letters* 34(34):5499–5502, 1993.
Herranz et al., "Solid Phase Synthesis of ψ[CH(CN)NH] Pseudopeptides. Application to the Synthesis of Analogues of Neurotensin [NT(8–13)]" *Tetrahedron Letters* 34(51):8357–8360, 1993.
Ho et al., "An Improved Low Racemization Solid–Phase Method for the Synthesis of Reduced Dipeptide (ψCH$_2$NH) Bond Isosteres" *Peptide Research* 6(1):10–12, 1993.
Bray et al., "Rapid Optimization of Organic Reactions on Solid Phase Using the Multipin Approach: Synthesis of 4–Aminoproline Analogues by Reductive Amination" *Tetrahedron Letters* 36(28):5081–5084, 1995.

Boojamra et al., "An Expedient and High Yielding Method for the Solid–Phase Synthesis of Diverse 1,4–Benzodiazepine–2,5–diones" *J. Org. Chem.* 60(18):5742–5743, 1995.
Chenera et al., "Protodetachable Arysilane Polymer Linkages for Use in Solid Phase Organic synthesis" *J. Am. Chem. Soc.* 117:11999–12000, 1995.
Ley et al., "Solid Phase Synthesis of Bicyclo[2.2.2]octane Derivatives via Tandem Michale Addition Reactions and Subsequent Reductive Amination" *SYNLETT* pp. 1017–1020, Oct., 1995.
Boojamra et al., "Solid–Phase Synthesis of ,4–Benzodiazepine–2,5–diones. Library Preparation and Demonstration of Synthesis Generality" *J. Org. Chem. J. Org. Chem.* 62:1240–1256, 1997.
Swayze, "The Solid Phase Synthesis of Trisubstituted 1,4–Diazabicyclo[4.3.0]nonan–2–one Scaffolds: On Bead Monitoring of Heterocycle Forming Reaction Using $^{15}N$ NMR" *Tetrahedron Letters* 38(10):8643–8646, 1997.
Sarantakis and Bicksler, "Solid Phase Synthesis of Sec–Amides and Removal from the Polymeric Support Under Mild Conditions" *Tetrahedron Letters* 38(42):7325–7328, 1997.
Holmes, "Model Studies for New o–Nitrobenzyl Photolabile Linkers: Substituent Effects on the Rates of Photochemical Cleavage" *J. Org. Chem.* 2370–2380, 1997.
Kenner et al., "The Safety Catch Principle in Solid Phase Peptide Synthesis" *J. Chemical Soc. Chem. Commun.* pp. 636–637, 1971.
Gallop et al., "Applications of Combinatorial Technologies to Drug Discovery" *J. Medicinal Chemistry* 37(9):1233–1251, Apr., 1994.
Gennari et al., "Solid–Phase Synthesis of Vinylogous Sulfonyl Peptides" *Angew. Chem. Int. Ed. Engl.* 34(16):1763–1765, 1995.
Look et al., "Trimethylorthoformate: A Mild and Effective Dehydrating Reagent for Solution and Solid Phase Imine Formation" *Tetrahedron Letters* 36(17):2937–2940, 1995.
AbdelMagid et al., "Reductive Amination of Aldehyde and Ketones with Sodium Triacetoxyborohydride. Studies on Direct and Indirect Reductive Amination Procedures" *J. Org. Chem.* 61:3849–3862, 1996.
Han et al., "Preparation and Applications of Xanthenylamide (XAL) Handles for Solid–Phase Synthesis of C–Terminal Peptide Amides Under Particularly Mild Conditions" *J. Org. Chem.* 61:6326–6339, 1996.
Beaver et al., "Application of the Sulfonamide Functional Group as an Anchor for Solid Phase Organic Synthesis (SPOS)" *Tetrahedron Letters* 37(8):1145–1148, 1996.

*Primary Examiner*—Shailendra Kumar
*Attorney, Agent, or Firm*—Christopher J. Smith; Leigh Firestone; Robert P. Blackburn

[57] ABSTRACT

Methods for solid phase synthesis of N-alkyl amides comprise reductive amination of carbonyl compounds using a reducing agent and an amine-containing linker bound to a solid support. The methods afford high yields of linker-bound, monoalkylated amines, and subsequent coupling with acid derivatives provide derivatized N-substituted amides in excellent yields after cleavage from the solid-phase. Compositions useful in solid phase synthesis are also described.

13 Claims, 1 Drawing Sheet

SOLID-PHASE SYNTHESIS OF N-ALKYL AMIDES

FIELD OF THE INVENTION

The present invention relates generally to methods and compositions for solid phase synthesis, and, more particularly, to methods and compositions for solid-phase synthesis of N-alkyl amides.

BACKGROUND OF THE INVENTION

Combinatorial chemistry has become a powerful tool for drug discovery in the pharmaceutical and biotechnology industries. Generally speaking, combinatorial chemistry is defined as the repetitive and systematic covalent attachment of different structural moieties to one another to produce a mixture of numerous distinct molecular entities or target molecules (i.e., combinatorial libraries); desired target molecules include peptides, oligonucleotides, and small organic molecules. Frequently, combinatorial chemistry is utilized to generate a group of structurally related analogs which can then be evaluated to establish structure-activity relationships (SAR) and to optimize biological potency. [See, e.g., M. A. Gallop et al., J. Med. Chem., 37:1233–1248 (1994)].

Solid supports (e.g., polystyrene resin beads and silica chips) and, concomitantly, solid phase synthesis techniques are routinely utilized in generating combinatorial libraries. Unfortunately, presently used techniques are associated with several limitations that restrict their efficiency and widespread application. One major limitation is the difficulty of producing target molecules that, following cleavage from the solid support, provide diverse functional groups at the carboxamide of the target molecules.

Researchers have had some recent successes in the development of chemical techniques that allow the production of a target molecule with particular functional groups at the carboxamide terminus following cleavage from the support. One such success relates to the generation of target molecules bearing sulfonamide functional groups. Previously, the use of linkers possessing a sulfur atom anchoring the target molecule to the resin (e.g., the so-called "safety-catch" linker [see, e.g., G. W. Kenner et al., J. Chem. Soc. Chem. Commun. 636 (1971)]) yielded only an acid or amide following cleavage of the sulfonyl peptide. [C. Gennari et aL, Angew. Chem. Int. Ed. Engl. 34:1763 (1995)]. However, new techniques involving the coupling of sulfonyl chlorides to an amino functionalized resin afford target molecules possessing a sulfonamide group at the carboxamide terminus of the molecules after cleavage. [K. A. Beaver et al., Tetrahedron Letters 37(8):1145–48 (1996)].

Despite recent developments in the field of solid-phase organic synthesis applications [see, e.g., Y. Han et al., J. Org. Chem. 61:6226–6339 (1996); T. L. Boehm et al., J. Org. Chem, 61:6498–6499 (1996)], there is presently no efficient technique for producing target molecules possessing an N-alkyl amide (e.g., RCONHR') at the carboxamide termini of the molecules following cleavage from the solid support. Indeed, the only method routinely used for the solid-phase synthesis of N-alkyl amides involves the aminolysis of resin-bound esters. However, this procedure requires an excess of amine for the aminolysis step [see, e.g., A. F. Abdel-Magid et al., J. Org. Chem. 61:3849–3862 (1996)], necessitating a subsequent purification procedure. Moreover, when utilizing this procedure, the target molecule must be anchored to the solid phase by an ester linkage rather than an amide linkage; unfortunately, the acid- and base- sensitivity of the ester limits the types of chemistry which can be used to modify the tethered target molecule.

Rink's amide resin has been extensively used for the solid-phase synthesis of peptide fragments, as it affords carboxamide primary amides ($RCONH_2$) upon cleavage from a substituted benzyhydryl amine linked to a polystyrene resin. [H. Rink, Tetrahedron Letters 28:3787–3790 (1987)]. Although the Rink amide resin is useful for the synthesis of primary amides [see, e.g., G. C. Look et al., Tetrahedron Letters 36:2937–2940 (1995)], there are no reported methods for the direct alkylation of the Rink amide resin or amine resin to facilitate the incorporation of a secondary amide, thus yielding concomitant diversity at the resin-bound position.

Resin-bound amines distinct from Rink's amine resin have been alkylated by a reductive amination procedure. For example, Mokotoff et al. [J. Med. Chem. 35:4696–4703 (1992)] reported the reaction of benzhydrylamine (BHA) resins directly with Boc-leucinal (in DMF containing 1% acetic acid), followed by reduction utilizing a solution of sodium cyanoborohydride (in DMF containing 1% acetic acid). However, the Mokotoff et al. procedure does not efficiently render N-alkylated amides in appreciable yields.

What is needed are methods and compositions for generating molecules containing a nitrogen-substituted amide at their amide termini (ie., that end of the molecules bound to the support) upon cleavage from a solid support. Such methods and compositions should allow for the production in high yields of target molecules with particular functional groups at their amide (e.g., carboxamide) termini.

SUMMARY OF THE INVENTION

The present invention relates generally to methods and compositions for solid phase synthesis, and, more particularly, to methods and compositions for solid-phase synthesis of N-alkyl amides. The methods of the present invention utilize a solvent system distinct from that used in conventional reductive alkylation reactions. More specifically, the reductive alkylation reactions contemplated by the present invention utilize a solvent system comprising aqueous solutions of THF or a related solvent, rather than the anhydrous conditions utilized in conventional reactions.

The methods of the present invention enable the efficient generation of peptides and other amide-derived products which bear an alkylated amide at the amide terminus of the molecule following cleavage from the support. The methods of the present invention may be used to generate diverse N-substituted amide derivatives, including carboxamides, sulfonamides, and phosphonamides, which, in turn, may be used in the formation of combinatorial libraries of compounds that can subsequently be screened for biological activity in order to provide information regarding structure-activity relationships. In addition, the methods provide a tool for the chemoselective, efficient installation of difunctional amines or other multifunctional amines on polystyrene resin or other solid supports.

In one embodiment, the compositions of the present invention comprise 4-(aminomethyl)-benzaldehyde linked via the amine group to a solid support (e.g., a polystyrene resin). The compositions allow chemistry to be performed on each functional group (i.e., the amine and the aldehyde) independently without polymerization between the groups.

In other embodiments, the present invention contemplates Rink's amide resin, through chemical manipulation of the corresponding amine, to be used in a straightforward deprotection/reductive alkylation procedure.

It should be emphasized that the methods of the present invention can be employed with other resins and with other linkers. For example, the methods of the present invention contemplate the use of other benzhydrylamine or methylbenzhydrylamine (MBHA) linkers on polystyrene resins, and Rink Linker, benzhydrylamine or methylbenzhydrylamine linkers on polyethylene glycol (e.g., polyethylene glycol resins or gels).

Specifically, the present invention contemplates a method for the solid phase synthesis of an N-substituted amide product, comprising: a) providing: i) a carbonyl compound, ii) a linker bound to a solid support, the solid support-bound linker comprising at least one amine group, iii) a reducing agent, and iv) an aqueous solvent system; b) reacting the amine group of the solid support-bound linker with the carbonyl compound and the reducing agent, the reaction occurring in the presence of the aqueous solvent system and yielding an N-alkylated solid support-bound linker; and c) treating the N-alkylated solid support-bound linker, thereby generating an N-substituted amide product.

In particular embodiments, the linker is selected from the group consisting of benzhydrylamine, benzhydrylamine derivatives, methylbenzhydrylamine and methylbenzhydrylamine derivatives. In some embodiments, the solid support-bound linker is 4-[(2',4'-dimethoxyphenyl)-aminomethyl]-phenoxymethyl-linked polystyrene resin. In certain embodiments, the carbonyl compound is selected from the group consisting of aldehydes and ketones.

In some embodiments of the present invention, the reducing agent is a hydride reducing agent, and the hydride reducing agent is sodium cyanoborohydride in still other embodiments. In particular embodiments, the aqueous solvent system comprises a compound from the group consisting of ρ-dioxane, tetrahydropyran, ethanol, methanol, isopropanol, propanol, N,N-dimethylformamide, N,N-dimethylacetamide, acetamide, N,N,N',N'-tetramethyl urea, N-methylpyrrolidinone, 2-ethoxyethanol, glyme, diglyme, and tetrahydrofuran. In further embodiments, the aqueous solvent system comprises an oxidation inhibitor.

In certain embodiments, the reacting step is a reductive alkylation, and in other embodiments, the treating step comprises acylating the N-alkylated solid support with a compound selected from the group consisting of acid halides (e.g., acid chlorides), acid anhydrides, and o-acyl isoureas.

The present invention also contemplates a method for the solid phase synthesis of an N-substituted carboxamide product, comprising: a) providing: i) a carbonyl compound, ii) a linker bound to a solid support, the solid support-bound linker comprising at least one amine group, iii) a reducing agent, and iv) an aqueous solvent system; b) reductively alkylating the solid support-bound amine linker with the carbonyl compound and the reducing agent, the reductive alkylation occurring in the presence of the aqueous solvent system and yielding an N-alkylated solid support-bound linker; c) either acylating the N-alkylated solid support-bound linker, thereby generating an N-alkylated solid-support bound amide, or sulfonylating the N-alkylated solid support-bound linker, thereby generating an N-alkylated solid-support bound sulfonamide; and d) cleaving the N-alkylated solid support bound amide or sulfonamide, thereby generating the N-substituted carboxamide product or sulfonamide product, respectively.

In particular embodiments, the linker is selected from the group consisting of benzhydrylamine, benzhydrylamine derivatives, methylbenzhydrylamine and methylbenzhydrylamine derivatives. In additional embodiments, the solid support-bound linker is 4-[(2',4'-dimethoxyphenyl)-aminomethyl]-phenoxymethyl-linked polystyrene resin. In further embodiments, the carbonyl compound is selected from the group consisting of aldehydes and ketones. In still further embodiments, the reducing agent is a hydride reducing agent, and the hydride reducing agent in sodium cyanoborohydride is still other embodiments.

In some of the embodiments involving acylation, the acylating agent is selected from the group consisting of acid chlorides and acid anhydrides. Similarly, in some embodiments involving sulfonylation, the sulfonylating agent is a sulfonyl chloride. In further embodiments, the solvent system comprises a compound selected from the group consisting of N,N-dimethylformamide and tetrahydrofuran, while in still further embodiments, the aqueous solvent system comprises an oxidation inhibitor.

The present invention also contemplates compositions comprising 4(aminomethyl)-benzaldehyde linked to a solid support. In some embodiments, the solid support is a resin, and in further embodiments the resin is a polystyrene resin.

DEFINITIONS

To facilitate understanding of the invention set forth in the disclosure that follows, a number of terms are defined below.

The terms "Rink's amide resin" and "Rink's Fmoc-protected amide resin" refer to 4-[(2',4'-dimethoxyphenyl)-(9-fluorenylmethyloxycarbonyl)aminomethyl] phenoxymethyl-linked polystyrene resin (depicted as structure 1 in FIG. 1), which is commercially-available from several sources (e.g., Novabiochem; Sigma). By comparison, the term "Rink's amine resin" refers to the Fmoc-deprotected form of Rink's amide resin (ie., 4-[(2',4'-dimethoxyphenyl)-aminomethyl]-phenoxymethyl-linked polystyrene resin) (depicted as structure 2 in FIG. 1).

The term "linker" refers to an anchoring group that serves to anchor or tether a growing target molecule to a solid support (e.g., polystyrene resin) during solid phase synthesis. Desirable characteristics of linkers may include, for example, lability to particular acid or base conditions (although very high sensitivity to acids or bases is typically not desirable). The linker is often the point of cleavage following synthesis; as such, chemical groups on the linker can become functional groups of the cleaved target molecule. The terms "Rink's amine linker," "Rink's linker," and the like refer to the 4-[(2',4'-dimethoxyphenyl)-aminomethyl]-phenoxymethyl- component of Rink's amine resin that is typically bound to polystyrene resin.

The term "solid support" refers broadly to supports used in the solid phase synthesis of, for example, peptides, nucleic acids, oligonucleotides, and small organic molecules. Solid supports include, but are not limited to, polymer resins (e.g., polyethylene glycol and polystyrene), gels (e.g., polyethylene glycol gels), polyacrylamide/ polyethylene glycol copolymer resins (e.g., RAPP polymer resin, NOVASYN® PEG A (Calbiochem-Novabiochem)), controlled pore glass supports (e.g., the CPG supports commercially available from Millipore), and silica beads and wafers.

The terms "carbonyl compound," "carbonyl," and the like refer to compounds containing the carbonyl functional group, C=O, which is present in aldehydes and ketones.

The terms "carboxamide terminus," "carboxamide termini," and the like refer to an end of a target molecule, synthesized by solid phase techniques and containing an —NHCO-group, that was covalently attached to a solid support (through, e.g., a linker) prior to cleavage. Analogously, the terms "sulfonamide terminus" and "phosphonamide terminus" refer to an end of a target molecule, synthesized by solid phase techniques and containing an —SO$_2$NH—group or an —PONH—group, respectively, that was covalently attached to a solid support (through, e.g., a linker) prior to cleavage.

The terms "reductive amination" and "reductive alkylation" refer broadly to the reactions of aldehydes or ketones (i.e., carbonyl compounds) with ammonia, primary amines, or secondary amines in the presence of reducing agents to yield primary, secondary, or tertiary amines, respectively; as used hereafter, reductive amination most frequently refers to reactions of primary amines to yield secondary amines. Carbonyl compounds are reductively aminated, while amines are reductively alkylated. While the present invention can be practiced with success without an understanding of the precise mechanism, it is believed that these reactions entail the initial formation of an intermediate carbinol amine derivative, which subsequently dehydrates to form an imine. Thereafter, the imine is protonated to produce an iminium ion, which is then reduced to yield the alkylated amine product (i.e., an N-alkyl amine). There are two general types of reductive amination reactions, indirect (or stepwise) and direct. Direct reactions do not entail prior formation of the intermediate imine when the carbonyl compound and the amine are combined with an appropriate reducing agent. Conversely, indirect reactions entail the formation of the intermediate imine in a distinct step prior to the reduction. [See, e.g., A. F. Abdel-Magid et al., J. Org. Chem. 61:3849-3862 (1996)]. The methods of the present invention may be employed with either direct or indirect reactions, but are preferably used in conjunction with direct reactions.

The term "solvent" refers to a liquid compound that is used to dissolve solids, liquids, or gases without reacting with them (unless desired) to bring the reaction components into close chemical proximity. Generally speaking, in a solution consisting of several components, the component present in excess is deemed to be the solvent. The term "organic solvent" refers broadly to solvents comprising carbon-containing molecules.

The term "solvent system" refers to a solution comprising a solvent and at least one other component; for example, a solvent system may comprise tetrahydrofuran, acetic acid, and water. The term "aqueous solvent system" refers to a solvent system comprising at least 3 parts (of 100 parts of a reaction mixture on a volume basis) water, more preferably greater than 5 parts water, and preferably less than 30 parts water.

The term "reducing agent" refers broadly to a compound (or a combination of compounds) which furnishes electrons to another. The term "hydride reducing agent" refers broadly to those reducing agents that comprise a hydrogen which assumes a negative charge (e.g., sodium borohydride and lithium aluminum hydride). A preferred hydride reducing agent of the present invention is sodium cyanoborohydride.

The term "acylating agent" refers to compounds comprising acyl groups (i.e. RCOX), paired functional groups in which a carbonyl is joined to "X", which may be oxygen, nitrogen, halogen, sulfur, or other electronegative atoms. Acylating agents include, but are not limited to, "acid halides" (e.g., acid chlorides like acetyl chloride and propionyl chloride, acid fluorides, and acid bromides) and "acid anhydrides" (e.g., acetic anhydride and formic acetic anhydride); the term "acid anhydride" refers to symmetrical, asymmetrical, and mixed anhydrides. In addition, acylating agents encompass both in situ-generated o-acyl isoureas, compounds produced from the reaction of an acid (e.g., bromoacetic acid) and a carbodimide (e.g., DIC and DCC).

and isolated o-acyl isoureas. The terms "acylation," "acylating," and the like refer to a chemical reaction whereby an acyl group is added to another moiety.

The terms "sulfonylation," "sulfonylating," and the like refer broadly to the addition of a sulfonyl group to another moiety. For example, phenol derivatives may be treated with benzene sulfonyl chloride and pyridine, resulting in the replacement of the hydroxyl hydrogen by the sulfonyl group. The term "sulfonyl chloride" refers to an agent, useful in effecting sulfonylation, that contains RSO$_2$Cl. Sulfonyl chlorides react with primary or secondary amines to render sulfonamides.

The terms "benzhydrylamine derivatives" and "methylbenzhydrylamine derivatives" refer to chemical compounds produced from benzhydrylamine and methylbenzhydrylamine (i.e., the parent compounds), respectively, in order to produce another compound of similar structure (e.g., through the replacement of a hydrogen atom with an alkyl or acyl group); the compound produced retains most of the functional features of the parent compound.

The terms "antioxidant," "oxidation inhibitor," and the like refer to an agent that inhibits oxidation (i.e., the chemical reaction whereby electrons are removed from atoms of the substances being oxidized and transferred to those being reduced). Oxidation inhibitors include, but are not limited to, butylated hydroxytoluene (BHT), and propyl gallate. BHT is a preferred oxidation inhibitor.

The terms "N-alkyl amide," "N-substituted amide," is meant to encompass compounds including, but not limited to, carboxamides, sulfonamides, and phosphonamides.

DESCRIPTION OF THE INVENTION

The present invention relates generally to methods and compositions for solid phase synthesis, and, more particularly, to methods and compositions for solid-phase synthesis of N-alkyl amides. Specifically, the present invention contemplates the use of specific reaction conditions in conjunction with solid supports containing modified acid-labile linkers to yield N-alkylated amides upon cleavage from the solid support.

METHODS

The methods of the present invention involve reductive amination under aqueous conditions. Use of these methods affords carboxamide termini-alkylated amides directly as amides following cleavage from the solid support. The methods of the present invention preferably utilize Rink's amide resin. However, the methods of the present invention may also be used in conjunction with other resins, including, but not limited to, the following commercially available (e.g., Calbiochem-Novabiochem) resins: benzhydrylamine (BHA) resin, methylbenzhydrylamine (MBHA) resin, 9-amino-xanthen-3-yloxy-Merrifield resin, NOVASYN® KR 125 resin (CalbiochemNovabiochem), NOVASYN® PR 500 resin (Calbiochem-Novabiochem), NOVASYN® TGR resin (Calbiochem-Novabiochem), Rink amide AM resin, Rink amide MBHA resin, NOVASYN® TG amino resin (Calbiochem-Novabiochem), NOVASYN® TG Sieber resin (Calbiochem-Novabiochem), and aminomethylated polystyrene resin. Of note, the use of NOVASYN® KR 125 resin (Calbiochem-Novabiochem), Sieber Amide resin (Calbiochem-Novabiochem), NOVASYN® PR 500 resin (Calbiochem-Novabiochem), Rink amide resin, Rink amide AM resin, and Rink amide MBHA resin require Fmoc deprotection as an initial step.

Moreover, the present invention contemplates the use of the linker component of Rink's amide resin with other solid supports (e.g., polyethylene glycol-based resins). In addition, other linkers (e.g., BHA and MBHA) bound to solid supports may be used with the methods of the present invention. The methods avoid the necessity of an aminolysis of the ester linkage using a large excess of reagents, as required by some of the methods discussed above.

The present invention entails a solvent system distinct from that used in conventional reductive alkylation reactions. More specifically, the reductive alkylation reactions contemplated by the present invention utilize a solvent system comprising aqueous solutions of THF or a related solvent, rather than the anhydrous conditions (e.g., 1% acetic acid in DMF or 1% acetic acid in methanol) employed in conventional reactions. In contrast to DMF, THF is not associated with amine-derived decomposition products which can compete with resin-supported amines for aldehyde during the reduction/alkylation process. The present invention also contemplates the addition of an oxidation inhibitor (e.g., BHT) to the THF solvent system in order to prevent any adverse effects that might result from the presence of THF-derived oxidation products in the reaction mixture.

As is the case for DMF, THF has several useful properties as a solvent for solid-phase synthesis. First, THF adequately swells the polystyrene resin. Second, it is an excellent co-solvent for many organic reactions, including reductive aminations using hydride reducing agents (e.g., sodium cyanoborohydride). Of course, the present invention is not limited to the use of a solvent system comprising THF. Preferred embodiments of the present invention contemplate the use of other organic solvents in an aqueous solvent system, including, but not limited to, ρ-dioxane, tetrahydropyran, ethanol, methanol, isopropanol, propanol, DMF, DMA, acetamide, N,N,N',N' tetramethyl urea, N-methylpyrrolidinone, 2-ethoxyethanol, glyme, and diglyme.

Most preferably, the present invention contemplates the use of a solvent system comprising aqueous acidified THF. When anhydrous conditions are used to alkylate the Rink linker directly, the reaction only proceeds to approximately 5 to 25% of completion during the first twenty-four hours. Though an understanding of the effect is not required in order to practice the present invention, it is believed that the presence of a small amount of water enables the rapid, complete reduction of the hindered in situ-generated iminium intermediates using sodium cyanoborohydride. Indeed, using most reagents, the presence of water results in the reaction to proceeding to over 90% completion in several hours. (See Table 1). In addition, the reaction can be run from −20° C. to 90° C. (in a sealed tube) as needed, depending upon the reactivity of the particular carbonyl compound being used.

In one embodiment of the present invention, commercially available Rink's amide resin (Calbiochem-Novabiochem) is first subjected to an Fmoc-deprotection reaction to yield Rink's amine resin. Standard deprotection conditions may be employed, including, for example, the use of a solution comprising 20% piperidine in DMF.

According to the methods of the present invention, Rink's amine resin is alkylated through a reductive amination reaction with an aldehyde or a ketone. The process can be stepwise or indirect (i.e., isolation of a resin-bound imine followed by reduction) or direct (i.e., addition of carbonyl compound and reduction in the same step).

Figure 1:
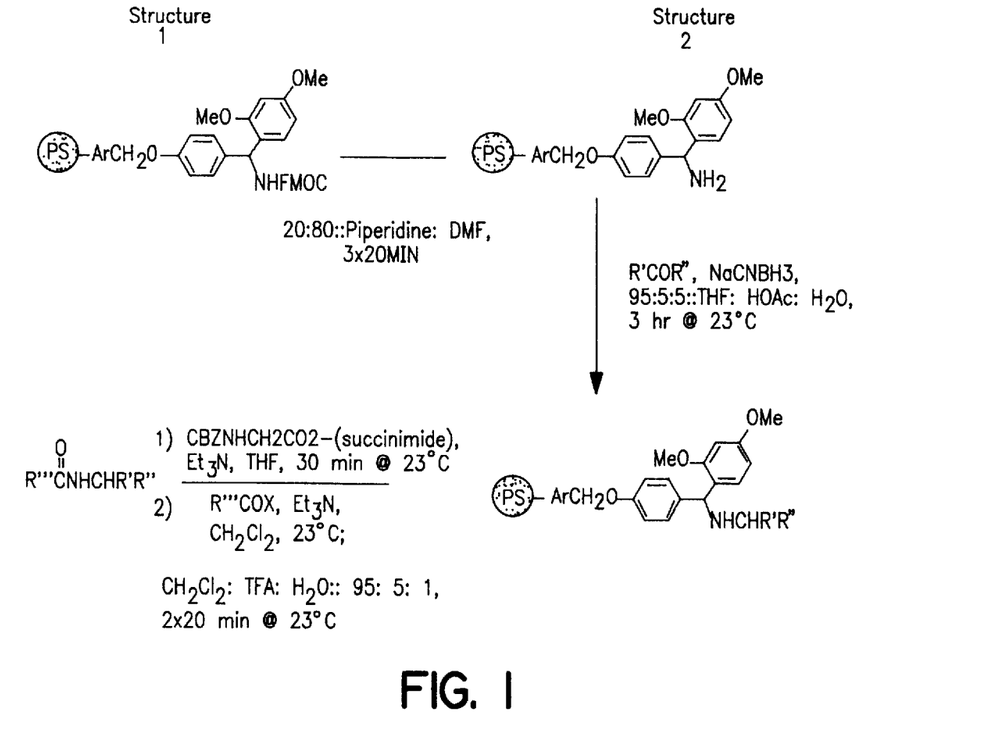
FIG. 1 depicts the synthetic scheme for the chemical synthesis of N-alkyl carboxamides from aromatic aldehydes and ketones according to a preferred embodiment of the present invention.

Equation 1 depicts the general direct chemical reaction using sodium cyanoborohydride as the reducing agent. The present invention contemplates the use of other hydride reducing agents, including, but not limited to, sodium triacetoxyborohydride. For stepwise reactions, sodium cyanoborohydride, sodium borohydride, lithium aluminum hydride, and borane are among the reducing agents that may be used. Similarly, the present invention contemplates the use of other reductive amination reagents, including, but not limited to, $Zn(BH_4)_2/ZnCl_2$.

(Equation 1)

where RINK-$NH_2$=Rink's amine resin; RINK-NH-CHRR'= Rink's alkylated resin; R=H, alkyl, aryl with various functional groups on alkyl/aryl; and R'=Me, alkyl, aryl.

The present invention is not limited by the nature of the carbonyl compounds incorporated. However, reactions wherein the carbonyl compound is ArCOR' usually proceed more slowly than reactions with other carbonyl compounds. Table 1 provides a representative list (under the heading "starting material") of some of the carbonyl compounds that have been successfully employed using the methods of the present invention.

Carbonyl compounds contemplated for use include, but are not limited to, acetaldehyde, propionaldehyde, buryraldehyde, pentanal, hexanal, diphenylacetaldehyde, 1-phenylpropanal, 2-phenylpropanal, phenylacetaldehyde, cyclohexanecarboxaldehyde, cyclopentanecarboxaldehyde, 2, 2-dimethylpropionaldehyde, 3-methylbutanal, 2-methylbutanal, 2-methoxy acetaldehyde, 2-methoxypropanal, 3-methoxypropanal, 4-hydroxybutanal, 5-hydroxypentanal, benzaldehyde, 1-naphthaldehyde, 2-naphthaldehyde, 4-hydroxy-1-naphthaldehyde, 4-phenylbenzaldehyde, 4-hydroxybenzaldehyde, 2-hydroxy-4-formylbenzoic acid, 4-(t-butyldimethylsilyloxy)benzaldehyde, 4-(t-butyldimethylsilyloxy)-3-methoxybenzaldehyde, 3-hydroxybenzaldehyde, 3-formylbenzoic acid, 4-formylbenzoic acid, 4-methoxybenzaldehyde, 3-methoxybenzaldehyde, 2-methoxybenzaldehyde, 4-ethoxybenzaldehyde, 3-ethoxybenzaldehyde, 2-ethoxybenzaldehyde, 4-allyloxybenzaldehyde, 3-allyloxybenzaldehyde, 2-allyloxybenzaldehyde, 4-benzyloxybenzaldehyde, 3-benzyloxybenzaldehyde, 2-benzyloxybenzaldehyde, 4-phenyloxybenzaldehyde, 3-phenyloxybenzaldehyde, 2-phenyloxybenzaldehyde, 3-(4-methoxy)phenyloxybenzaldehyde, 4-bromobenzaldehyde, 3-bromobenzaldehyde, 2-bromobenzaldehyde, 4-iodobenzaldehyde, 3-iodobenzaldehyde, 2-iodobenzaldehyde, 4-chlorobenzaldehyde, 3-chlorobenzaldehyde, 2-chlorobenzaldehyde, 4-fluorobenzaldehyde, 3-fluorobenzaldehyde, 2-fluorobenzaldehyde, 2,6-dichlorobenzaldehyde, 4-acetoxybenzaldehyde, 4-benzoyloxybenzaldehyde, 4-formylbenzaldehyde, 3-formylbenzaldehyde, 4-N,N-(dimethylamino)benzaldehyde, 4-nitrobenzaldehyde, 3-nitrobenzaldehyde, 4-carbomethoxybenzaldehyde, 4-fornyl cinnamic acid, 4-styrenecarboxaldehyde, 3,4-dimethoxybenzaldehyde, vanillin, ovanillin, 3-methoxy-4-acetoxybenzaldehyde, 3-methoxy-4-benzoyloxybenzaldehyde, 3,4-(methylenedioxy) benzaldehyde, 9-ethyl-3-carbazolecarboxaldehyde, 2-furaldehyde, 3-furaldehyde, 4-formyl-5-methylimidazole, 3-phenyl-4-formylpyrazole, 1-phenyl-2-propanone, 1-[3-(trifluoromethylphenyl)]-2-propanone, 1-(3,4-dimethoxyphenyl)-2-propanone, 1-[3,4-(methylenedioxy)]-2-propanone, cyclohexanone, cyclopentanone, 3-methyl-2-butanone, 7-ketooctanoic acid, 4-hydroxy-2-pentanone, 4-(4-hydroxyphenyl)2-butanone, 2-methoxyacetone, 4,4-dimethyl-2-pentanone, methyl-2-ketopropanoate, 6-methyl-hept-5-ene-2-one, and 4-(1-pyrazolyl)-2-butanone. Of note, products with free hydroxyl or primary and secondary amino groups usually are isolated as their acylated derivatives after TFA cleavage from the resin.

Rink's alkylated resin is then treated with an acylating agent to yield the resin-bound amide (Equation 2). Preferred acylating agents are reactive anhydrides and acid halides (e.g., acid chlorides, acid bromides, and acid fluorides), and more preferred acid halides are acid chlorides. Acid anhydrides contemplated by the present invention include, but are not limited to, acetic anhydride, trifluoroacetic anhydride, and benzoic anhydride. Acid chlorides contemplated by the present invention include, but are not limited to, acryloyl chloride, methacryloyl chloride, crotonoyl chloride, benzoyl chloride, cinnamoyl chloride, hydrocinnamoyl chloride, acetyl chloride, 2-acetoxyacetyl chloride, diphenylacetyl chloride, 2-methoxybenzoyl chloride, 3,4,5-trimethoxybenzoyl chloride, 3,4-(methylenedioxy)benzoyl chloride, cyclopropanecarbonyl chloride, pentadecanoyl chloride, 2-cyclohexene-1-carbonyl chloride, and 2-thiopheneacetyl chloride.

(Equation 2)

General mild cleavage conditions (e.g., trifluoroacetic acid and water in dichloromethane; see Equation 3) renders the desired N-alkyl amide product (i.e., target molecule):

(Equation 3)

For relatively unhindered acids, a carbodiimide and acid protocol can be used (e.g., $BrCH_2CO_2H+DIC/CH_2Cl_2$ at room temperature) involving the generation of o-acyl isoureas. Acids that may be employed using the carbodiimide method include, but are not limited to, bromoacetic acid, chloroacetic acid, and phenylacetic acid. Cleavage may then be effected as described above to render the desired N-alkyl amide product.

The methods of the present invention may be used to synthesize a broad range of N-alkyl amide compounds, including, but not limited to, $PhCH_2NHBz$, $PhCH_2NHCOCF_3$, $CH_3CH_2NHBz$, 4-(AcO)-3-(MeO)$PhCH_2NHBz$, 4-(CHO)-$PhCH_2NHBz$, and $PhCH_2NHCOCH_2Br$. Table 1 illustrates some of the aldehydes and ketones that may be used as starting materials, certain acylating agents that may be reacted with resin-bound derivatives of those starting materials, and the products (including yield and purity) produced using those reactants. In each of the reductive alkylation reactions, the solvent system comprised a mixture of $THF/H_2O/HOAc$ of 90:5:5.

TABLE 1

| Starting Material | Acylating Agent | Product | Yield | Purity |
|---|---|---|---|---|
| Br-C6H4-CHO (2-Br) | Benzoyl Chloride | 2-Br-C6H4-CH2-NH-C(O)-Ph | 95% | 98% |
| O2N-C6H4-CHO (3-NO2) | Benzoyl Chloride | 3-O2N-C6H4-CH2-NH-C(O)-Ph | 94% | 98% |
| MoO-C6H4-CHO (4-MoO) | Acetic Anhydride | 4-MoO-C6H4-CH2-NH-C(O)CH3 | 97% | 94% |
| C6H5-CHO | Pivaloyl Chloride | Ph-CH2-NH-C(O)C(CH3)3 | 77% | 85% |

TABLE 1-continued

| Starting Material | Acylating Agent | Product | Yield | Purity |
|---|---|---|---|---|
| 1-naphthaldehyde | Acetic Anhydride | N-(naphthalen-1-ylmethyl)acetamide | 85% | 97% |
| furan-2-carbaldehyde | Benzoyl Chloride | N-(furan-2-ylmethyl)benzamide | 50% | 80% |
| pivaldehyde | Benzoyl Chloride | N-neopentylbenzamide | 88% | 70% |
| cyclohexanone | Methacryloyl Chloride | N-cyclohexylmethacrylamide | 99% | 97% |

In preferred embodiments, the methods of the present invention are used to generate N-substituted carboxamides. In addition, the methods may be employed in the solid phase synthesis of other N-substituted amide derivatives, including, but not limited to, sulfonamides and phosphonamides. For example, as depicted in Equation 4, sulfonyl chlorides can be reacted with Rink's alkylated resin to yield resin-bound sulfonamides; preferred conditions include the use of, for example, chloroform: pyridine [50:50], 3 equivalents of a sulfonyl chloride, and heating for 40 hrs at reflux. Of course, the present invention contemplates the use of other reaction conditions to render resin-bound sulfonamides. Sulfonyl chlorides contemplated for use with the present invention include methanesulfonyl chloride, tosyl chloride, and trifluoromethanesulfonyl chloride.

(Equation 4)

RINK—NH—CHRR'

RINK—N[(SO$_2$R$^3$)(CHRR')]

Thereafter, conventional mild cleavage conditions may be used to render the desired sulfonamide product (Equation 5):

(Equation 5)

RINK—N[(SO$_2$R$^3$)(CHRR')]

R$^3$SO$_2$—NH—CHRR'

Of note, where the linked compound contains a tertiary amine group (e.g., pyridine derivatives or trialkylamines), generation of certain N-alkylated amides by cleavage from the solid support may be retarded under particular conditions. For example, whereas cleavage of an N-alkyl-3-pyridine-carboxamide derivative using CH$_2$Cl$_2$:TFA:H$_2$O 10:0.5:0.1 for 20 minutes yielded a small amount of product, cleavage of a derivative tertiary amine (a 1,3 pyridine di-acid derivative) from the linker under identical conditions afforded a 71% yield of desired material.

In one embodiment, the methods of the present invention are used in the efficient generation of peptides and other oligomeric molecules which bear an alkylated amide at the N-terminus of the molecule following cleavage from the support. More specifically, Rink's amine resin or another suitable support is used as the point of attachment for a growing oligomeric chain. Techniques known in the field of solid phase synthesis are used in chain elongation. After the desired chain has been generated, the methods of the present invention may be used to generate diverse N-substituted derivatives, including carboxamides, sulfonamides, and phosphonamides.

COMPOSITIONS

Figure 2:
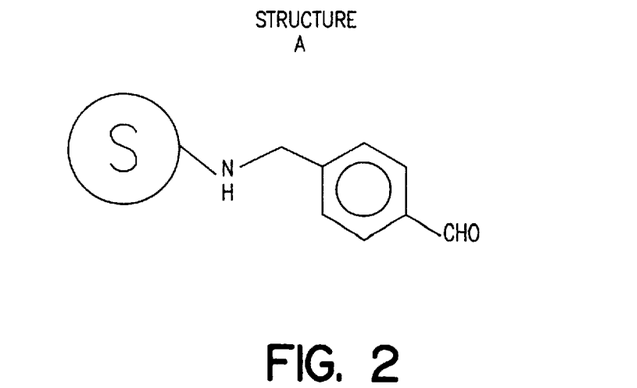
FIG. 2 depicts the structure of a composition of the present invention.

The present invention also contemplates compositions that are useful for solid phase synthesis. The compositions comprise 4-(aminomethyl)-benzaldehyde linked via the amine to a solid support (e.g., a polystyrene resin). FIG. 2 depicts the structure of 4-(aminomethyl)-benzaldehyde linked to a generic solid support "S".

The compositions are not limited by the nature of the solid support; indeed, any solid support to which the 4-(aminomethyl)-benzaldehyde linker group can be bound may be used in conjunction with the compositions of the present invention. Suitable solid supports include those resins previously discussed. In preferred embodiments, the solid support component of the compositions is a polystyrene-, polyethylene glycol-, or acrylamide-based resin. Preferably, resin loading is less than approximately 0.8 mmol/g, and most preferably greater than approximately 0.4 mmol/g for polystyrene-based resins.

Because the compositions comprise both an amino group and an aldehyde, they provide a useful starting point for performing additional solid phase chemistry. For example, the amine moiety of the compositions may be modified to produce N-alkyl amides. The carbonyl moiety of the compositions may be modified to produce alkenes, stilbenes, heterocycles, chalcones, imines, cyanohydrins, cyanoamine derivatives, alcohols, etc.

The uniqueness of the compositions is that i) the amine and carbonyl moieties cannot self-condense in an intramolecular fashion because of the rigidity of the ring structures and the 1- and 4- positioning of the pendent groups, and ii) condensation of pendent groups or linked groups in a pseudo-intramolecular fashion (i.e., the 4-(aminomethyl)-benzaldehyde groups are linked to a common solid support) is kinetically disfavored due to the hindrance and rigidity of the solid support. This is in contrast to the behavior of hypothetical solution phase 4-(aminomethyl)-benzaldehyde which is expected to rapidly self-condense and polymerize.

DESCRIPTION OF THE PREFERRED EMBODIMENT

FIG. 1 depicts the synthetic scheme for the chemical synthesis of N-alkyl amides from aromatic aldehydes and ketones according to the preferred embodiment of the present invention. As depicted in FIG. 1, Fmoc deprotection of the Rink amide resin is achieved through reaction with a mixture of piperidine and DMF. The resulting Rink amine resin is subjected to a reductive amination procedure using sodium cyanoborohydride in conjunction with a desired aldehyde or ketone. The present invention contemplates the use of mixtures of THF/$H_2$O/HOAc in a variety of ratios (based on volume), including, but not limited to, 96:3:1, 85:10:5, 75:10:15, and 60:20:20. In preferred embodiments, a mixture of THF/$H_2$O/HOAc of 90:5:5 provides rapid reaction rates for the selective mono-alkylation of Rink's amine resin with a variety of carbonyl derivatives. Other acids besides acetic acid may be used, including, but not limited to, propionic acid or benzoic acid.

When aromatic carbonyl compounds are employed, the mole ratio of amine loading on Rink's amide resin to carbonyl compound is preferably 1:1.1 to 1:10 (number of equivalents of Rink-$NH_2$ to RCOR'). By comparison, when aliphatic aldehydes are used, the ratios of starting materials are slightly different; more specifically, a mole ratio of Rink's amide resin loading to aliphatic carbonyl compound of 1:1.10 is preferred, and 1:1.05 is more preferred. Adjustment of the ratio of reactants is desired because larger amounts of aliphatic aldehyde frequently lead to reduced yields and impure products.

As determined from analysis of the ratios of $NH_2$Bz:NHRBz resulting from benzoylation of aliquots of crude resins, cleavage, and gas chromatography/mass spectroscopy analysis (results not shown), the alkylation reactions proceed nearly to completion (>95%) in approximately three hours at room temperature; however, the rates slow considerably after approximately 95% of the primary amine groups are alkylated. Though an understanding of why the reactions do not proceed to completion is not required in order to practice the present invention, it is presumably due to severe hindrance at the remaining 5% of amine sites. Because repeated reactions do not alkylate the remaining 2–5% of the Rink amine resin groups to any significant extent, the remaining primary amine positions may be capped using, for example, the selective acylating agent CBZ-glycine N-hydroxysuccinimide ester prior to acylation with anhydrides or acid chlorides. [M. Mokotoff et al., J. Med. Chem. 35:4696–4703 (1992)].

EXPERIMENTAL

The following examples serve to illustrate certain preferred embodiments and aspects of the present invention and are not to be construed as limiting the scope thereof.

In the experimental disclosure which follows, the following abbreviations apply: Eq and Eqs (equivalents); mEq (milliequivalents); M (molar); mM (millimolar) $\mu$M (micromolar); N (Normal); mol (moles); mmol (millimoles); $\mu$mol (micromoles); nmol (nanomoles); g (grams); mg (milligrams); $\mu$g (micrograms); Kg (kilograms); L (liters); mL (milliliters); $\mu$L(microliters); cm (centimeters); mm (millimeters); $\mu$m (micrometers); nm (nanometers); min. (minutes); s and sec. (seconds); ° C. (degrees Centigrade); BHA (benzhydrylamine); MBHA (methylbenzhydrylamine); BHT (butylated hydroxytoluene); CBZ (carbobenzyloxy); DMA (N,N-dimethylacetamide); DMF (N,N-dimethylformamide); HOAc (acetic acid); EtOH (ethanol); MeOH (methanol); $Et_3N$ (triethylamine); $CH_2Cl_2$ (dichloromethane); NaC-$NBH_3$ (sodium cyanoborohydride); PS (polystyrene); TFA (trifluoroacetic acid); THF (tetrahydrofuran); Fmoc (9-fluorenylmethyloxycarbonyl-); Rink's Fmoc-protected amide resin and Rink's amide resin (4-[(2',4'-dimethoxyphenyl)-(9-fluorenylmethyloxycarbonyl) aminomethyl]-phenoxymethyl-linked polystyrene resin); Rink's amine resin (4-[(2',4'-dimethoxyphenyl)-(aminomethyl)]-phenoxymethyl-linked polystyrene resin); Rink's amine linker and Rink's linker 4-[(2',4'-dimethoxyphenyl)-aminomethyl]-phenoxymethyl-component of Rink's amine resin; Ph (phenyl); GCMS (gas chromatography/mass spectroscopic analysis); HPLC (high pressure liquid chromatography); NMR (nuclear magnetic resonance); Aldrich (Aldrich Chemical Company, Milwaukee, Wis.); Calbiochem-Novabiochem (San Diego, Calif.); Millipore (Bedford, Mass.), and Sigma (Sigma Chemical Company, St. Louis, Mo.).

Unless otherwise indicated, in the examples that follow sureseal grade THF, piperidine, most carbonyl compounds, and $NaCNBH_3$ in THF were purchased from Aldrich and were used as received. Rinse solvents were purchased from Baxter and were used as received. Rink's amide resin (0.45–0.51 mmol/g, and generally 0.48 mmol/g) was purchased from Calbiochem-Novabiochem and was initially deprotected with 20%:80% :: piperidine:DMF before use. Products were characterized by comparison of $^1$H NMR, $^{13}$C NMR, and GCMS data with literature values. Purities were determined by HPLC with 214 nm monitoring wavelength.

As previously alluded to, contamination will occur if THF-derived oxidation products are present in the solvent. The THF utilized in the experiments described in the examples that follow was peroxide-free when tested with damp starch-iodine paper. The presence of an oxidation inhibitor (e.g., BHT) in the THF solvent solution neither appreciably nor adversely affects the reaction.

In each of the examples that follow, Fmoc deprotection of Rink's amide resin was performed as follows unless otherwise indicated. In a peptide synthesis reaction vessel was placed Rink's FMOC-protected amide resin (4-[(2',4'-dimethoxyphenyl)-(9-fluorenylmethyloxycarbonyl) aminomethyl]-phenoxymethyl-linked polystyrene resin) (0.48 mmol/g loading, 10 g, 4.8 mmol) (Calbiochem-Novabiochem). The material was deprotected using 20% piperidine in DMF (3×100 mL, 20 min each). Thereafter, the material was filtered washed in succession with DMF (3×100 mL), water, MeOH, $CH_2Cl_2$, and the material was then dried under vacuum at 70° C. for 24 hours. The deprotected, dried powder ("Rink amine resin") was subsequently used in each reductive amination reaction. Resin loading of Rink amine resins was determined to be 0.55 mEq/g by ninhydrin analysis. [V. K. Sarin et al., Anal. Biochem. 117:147–157 (1981)].

EXAMPLE 1

Synthesis of N-Benzyl Pivalamide Using A Solvent System Comprising Aqueous THF The experiment of this example illustrates the efficient synthesis via solid phase methods of a compound (N-benzyl pivalamide) containing an alkylated amide at its carboxamide terminus upon cleavage from the solid phase. The experiments of this example utilized a solvent system comprising aqueous THF.

Reductive Amination And Acylation

In a fritted reaction vessel was placed a mixture of Rink's amine resin (100 mg, 0.055 mmol), peroxide-free THF (1.0 mL), and benzaldehyde (7 µL, 0.067 mmol). To the reaction vessel was added 100 µl of 50:50 HOAC:water. After shaking for 5 minutes at 23° C., a 1M THF solution of NaCNBH$_3$ (50 µL, 50 µmol) was added (with mild effervescence). The vessel was sealed using a teflon-lined screw cap, and the resulting mixture was shaken for 3 hours at room temperature.

The reaction was worked up by filtration and washing the resin with, in succession, THF, H$_2$O, MeOH, THF and CH$_2$Cl$_2$ (2×1 mL each). The resin was then treated with a solution of CBZ-glycine N-hydroxysuccinimide ester (3.1 mg, 0.010 mmol) and triethylamine (4 µL, 0.033 mmol) in THF (1.0 mL) for 30 minutes to cap unalkylated resin-bound amine groups. The resin was filtered and washed as described in the preceding paragraph, and was then treated with a solution of triethylamine (400 µL, 2.9 mmol) and pivaloyl chloride (100 µL, 0.75 mmol) in CH$_2$Cl$_2$ (700 µL) for 3 hours at 23° C.

Cleavage

The resulting material was filtered washed in succession with DMF (3×100 µL), water, MeOH, CH$_2$Cl$_2$, and briefly air-dried to provide the resin as a tan solid. Cleavage of the amide material (N-benzyl pivalamide) from the resin was performed using 94:5:1 :: CH$_2$Cl$_2$:TFA:H$_2$O(2×700 µL, 20 min) as for typical peptide cleavages. After combining the cleavage filtrates and CH$_2$Cl$_2$ washings (3×500 µL), the solution was concentrated under vacuum to give an amber oil (8.1 mg, 77% yield). Purity, as judged by HPLC using detection at 214 nm, was 86%. $^1$H NMR (300 MHz, CDCl$_3$): 7.42–7.25 (m 5H), 6.05–5.87 (bs, 1H), 4.44 (d, 1H, J=7.2 Hz), 1.23 (s, 9H). $^{13}$C NMR (75 MHz, CDCl$_3$): 174, 138, 129, 128, 127.5, 43, 28, 27. ESMS: m/e=191, 176, 149, 106, 91, 57.

EXAMPLE 2

Synthesis of N-Benzyl Benzamide Using Solvent Systems Comprising Aqueous and Anhydrous DMF The experiments of this example compared different solvent systems for the synthesis via solid phase methods of N-benzyl benzamide. More specifically, the experiments of this example utilized either a conventional solvent system comprising 5% acetic acid/5% water in DMF, 1% acetic acid/1% water in DMF, or anhydrous 1% acetic acid in DMF.

A. Solvent System Comprising 5% Acetic acid/5% Water In DMF

In a fritted reaction vessel was placed a mixture of Rink's amine resin (50.2 mg, 0.024 mmol), DMF (1.0 mL), and benzaldehyde (15 µL, 0.14 mmol). To the reaction vessel was added 100 µL of 50:50 HOAC:water. After shaking for 5 minutes at 23° C., a 1M THF solution of NaCNBH$_3$ (50 µL, 50 µmol) was added (with mild effervescence). The vessel was sealed using a teflon-lined screw cap, and the resulting mixture was shaken for 2 hours at 23° C.

The reaction was worked up by filtration and washing the resin with, in succession, DMF, THF, H$_2$O, MeOH, THF and CH$_2$Cl$_2$ (2×1 mL each). The resin was filtered and washed as described in the preceding paragraph, and was then treated with a solution of triethylamine (200 µL, 1.45 mmol) and benzoyl chloride (100 µL, 0.86 mmol) in CH$_2$Cl$_2$ (1 mL) for 3 hours at 23° C.

The resulting resin was filtered and washed in succession with CH$_2$Cl$_2$, THF, H$_2$O, MeOH, THF and CH$_2$Cl$_2$ (2×1 mL each) and briefly air-dried to provide the resin as a tan solid. Cleavage of the amide material from the resin was performed using 94:5:1 :: CH$_2$Cl$_2$:TFA:H$_2$O(2×700 µL, 20 min) as for typical peptide cleavages. After combining the cleavage filtrates and CH$_2$Cl$_2$ washings (3×500 µL), the solution was concentrated under vacuum to give a yellow oil (4.8 mg, 86% yield).

B. Solvent System Comprising 1% Acetic Acid/1% Water In DMF

This experiment was performed analogously to that set forth in part A, except that 20 µL (rather than 100 µL) of a 50:50 HOAC:water mixture was used as the solvent system. Following workup and cleavage, N-benzyl benzamide was afforded as a colorless oil (1.4 mg, 25% yield).

C. Anhydrous Solvent System Comprising 1% Acetic Acid In DMF

This experiment was performed analogously to that set forth in part A, except that 10 µL of anhydrous acetic acid were used as the solvent system. Following workup and cleavage, N-benzyl benzamide was afforded as a colorless oil (1.4 mg, 25% yield).

The experiments of this example indicate that the aqueous solvent system used in the experiment of part A afforded the desired N-alkylated product in appreciably greater yield than the anhydrous solvent system used in part C. In addition, use of a larger amount of water in the aqueous solvent system provided a much higher yield of the desired product.

EXAMPLE 3

Synthesis of N-(ρ-Benzyloxybenzyl) Acetamide Using A Solvent System Comprising Aqueous and Anhydrous THF The experiments of this example compare two different solvent systems for the generation of N-(ρ-benzyloxybenzyl)-acetamide following cleavage from the solid support. The experiments of this example utilized either a conventional solvent system comprising THF in anhydrous 1% acetic acid or THF in 1% acetic acid under hydrated conditions to generate an alkylated resin-bound intermediate. The alkylated resin-bound intermediate was then treated with a reactive anhydride, affording the desired product.

A. Aqueous Solvent System

In a fritted reaction vessel was placed a mixture of Rink's amine resin (100 mg, 0.055 mmol), peroxide-free THF (1.0 mL), and ρ-benzyloxybenzaldehyde (15 mg, 0.071 mmol). To the reaction vessel was added 120 μL of 50:50 HOAC::water. After shaking for 5 minutes at 23° C., a 1M THF solution of NaCNBH$_3$ (500 μL, 500 μmol) was added (with mild effervescence). The vessel was sealed using a teflon-lined screw cap, and the resulting mixture was shaken for 84 hours at 65° C. The vessel was cooled to room temperature and opened slowly to release the built-up pressure.

The reaction was worked up by filtration and washing the resin with, in succession, THF, H$_2$O, MeOH, THF and CH$_2$Cl$_2$ (2×1 mL each). The reaction was then treated with a solution of triethylamine (500 μL, 3.61 mmol) and acetic anhydride (300 μL, 3.17 mmol) in CH$_2$Cl$_2$ (3 mL) for 3 hours at 23° C.

The resulting resin was filtered and washed in succession with CH$_2$Cl$_2$, THF, H$_2$O, MeOH, THF and CH$_2$Cl$_2$ (2×1 mL each) and briefly air-dried to provide the resin as a tan solid. Cleavage of the amide material from the resin was performed using 94:5:1 :: CH$_2$Cl$_2$:TFA:H$_2$O (2×700 μL, 20 min) as for typical peptide cleavages. After combining the cleavage filtrates and CH$_2$Cl$_2$ washings (3×500 μL), the solution was concentrated under vacuum to give a white solid (9.2 mg, 85% yield).

B. Anhydrous Solvent System

This experiment was performed analogously to that set forth in part A, except that 60 μL of acetic acid (rather than 120 μL of a 50:50 HOAC:water mixture) was used as the solvent system. Following workup and cleavage, N-(ρ-Benzyloxybenzyl) acetamide was afforded as a colorless oil (1.1 mg, 12% yield).

The experiments of this example indicate that the aqueous solvent system afforded the desired product in appreciably greater yield than the anhydrous solvent system.

EXAMPLE 4

Composition Synthesis

As set forth above, the present invention contemplates compositions comprising 4-(aminomethyl)-benzaldehyde linked via the amine group to a solid support (e.g., a polystyrene resin). The compositions may be produced by utilizing the general procedures outlined above relating to reductive amination.

Briefly, in a fritted reaction vessel was placed a mixture of Rink's amine resin (5.00 g, 2.40 mmol), THF (60 mL), and ρ-formylbenzaldehyde (970 mg, 7.20 mmol). To the reaction vessel was added 3.0 mL of water and 3.0 mL of acetic acid. After shaking for 10 minutes at 23° C., a 0.55M THF solution of NaCNBH$_3$ (1.60 mL, 0.88 mmol) was added (with mild effervescence). The vessel was sealed using a teflon-lined screw cap, and the resulting mixture was shaken for 6 hours at 23° C.

The reaction was worked up by filtration and washing the resin with, in succession, THF, H$_2$O, MeOH, THF and CH$_2$Cl$_2$ (3×60 mL each). The resin was dried in vacuo for 24 hours, rendering a tan powder containing both amine and carbonyl functionality.

Based upon the preceding discussion and experimental materials, it should be clear that the present invention provides efficient methods for the preparation of a product bearing an alkylated amine at its resin-bound terminus (e.g., carboxamide terminus) upon cleavage from the solid phase. In addition, compositions are disclosed that are useful in solid phase synthesis procedures.

We claim:

1. A method for the solid phase synthesis of an N-substituted amide product, comprising:

a) providing: i) a carbonyl compound, ii) a linker bound to a solid support, said solid support-bound linker comprising at least one amine group, iii) a reducing agent, and iv) an aqueous solvent system;

b) reacting said amine group of said solid support-bound linker with said carbonyl compound and said reducing agent, said reaction occurring in the presence of said aqueous solvent system and yielding an N-alkylated solid support-bound linker; and c) treating said N-alkylated solid support-bound linker, thereby generating said N-substituted amide product.

2. The method of claim 1, wherein said linker is selected from the group consisting of benzhydrylamine, benzhydrylamine derivatives, methylbenzhydrylamine and methylbenzdrylamine derivatives.

3. The method of claim 1, wherein said solid support-bound linker is 4[(2',4'-dimethoxyphenyl)-aminomethyl]-phenoxymethyl-linked polystyrene resin.

4. The method of claim 1, wherein said carbonyl compound is selected from the group consisting of aldehydes and ketones.

5. The method of claim 1, wherein said reducing agent is a hydride reducing agent.

6. The method of claim 5, wherein said hydride reducing agent is sodium cyanoborohydride.

7. The method of claim 1, wherein said aqueous solvent system comprises a compound from the group consisting of ρ-dioxane, tetrahydropyran, ethanol, methanol, isopropanol, propanol, N,N-dimethylformamide, N,N-dimethylacetamide, acetamide, N,N,N',N'-tetramethyl urea, N-methylpyrrolidinone, 2-ethoxyethanol, glyme, diglyme, and tetrahydrofuran.

8. The method of claim 1, wherein said aqueous solvent system comprises an oxidation inhibitor.

9. The method of claim 1, wherein said reacting step is a reductive alkylation.

10. The method of claim 1, wherein said treating step comprises acylating said N-alkylated solid support with a compound selected from the group consisting of acid chlorides and acid anhydrides.

11. The method of claim 1, wherein step (c) includes cleavage of the product from the support under mild cleavage conditions.

12. The method of claim 11, wherein the mild cleavage conditions comprise exposure to trifluoroacetic acid and water in dichloromethane, or a carbodiimide and an acid at room temperature.

13. The method of claim 12, wherein the acid is selected from the group consisting of bromoacetic acid, chloroacetic acid, and phenylacetic acid.

* * * * *